United States Patent [19]

Southard

[11] Patent Number: 5,197,981
[45] Date of Patent: Mar. 30, 1993

[54] INTRAOCULAR LENS HAVING HAPTIC OF SPECIFIC CURVATURE AND PROPORTION

[75] Inventor: Michael A. Southard, Arlington, Tex.
[73] Assignee: Alcon Surgical, Inc., Fort Worth, Tex.
[21] Appl. No.: 872,937
[22] Filed: Apr. 23, 1992
[51] Int. Cl.⁵ ............................................. A61F 2/16
[52] U.S. Cl. .................................................. 623/6
[58] Field of Search ............................................. 623/6

[56] References Cited

U.S. PATENT DOCUMENTS

| | | | |
|---|---|---|---|
| Re. 33,039 | 8/1989 | Arnott | 623/6 |
| 4,174,543 | 11/1979 | Kelman | 623/6 |
| 4,268,921 | 5/1981 | Kelman | 623/6 |
| 4,418,431 | 12/1983 | Feaster | 623/6 |
| 4,446,581 | 5/1984 | Blake | 623/6 |
| 4,504,981 | 3/1985 | Walman | 623/6 |
| 4,568,347 | 2/1986 | Reichert, Jr. | 623/6 |
| 4,575,374 | 3/1986 | Anis | 623/6 |
| 4,581,033 | 4/1986 | Callahan | 623/6 |
| 4,585,455 | 4/1986 | Blackmore et al. | 623/6 |
| 4,591,358 | 5/1986 | Kelman | 623/6 |
| 4,608,049 | 8/1986 | Kelman | 623/6 |
| 4,655,775 | 4/1987 | Clasby, III | 623/6 |
| 4,664,665 | 5/1987 | Reuss et al. | 623/6 |
| 4,664,667 | 5/1987 | Kelman | 623/6 |
| 4,676,794 | 6/1987 | Kelman | 623/6 |
| 4,701,181 | 10/1987 | Arnott | 623/6 |
| 4,710,195 | 12/1987 | Giovinazzo | 623/6 |
| 4,725,277 | 2/1988 | Bissonette | 623/6 |
| 4,731,079 | 3/1988 | Stoy | 623/6 |
| 4,816,031 | 3/1989 | Pfoff | 623/6 |
| 4,822,358 | 4/1989 | Jaffe | 623/6 |
| 4,828,558 | 5/1989 | Kelman | 623/6 |
| 4,863,465 | 9/1989 | Kelman | 623/6 |
| 4,871,363 | 10/1989 | Kelman | 623/6 |
| 4,923,468 | 5/1990 | Wild | 623/6 |
| 4,932,967 | 6/1990 | Kansas | 623/6 |
| 4,990,159 | 2/1991 | Kraff | 623/6 |

FOREIGN PATENT DOCUMENTS 2111835 7/1983 United Kingdom ...................... 623/6

OTHER PUBLICATIONS

Article entitled *In search of the ideal IOL, Structural features designed for capsular-bag placement*, James A. Davison, MD, Ocular Surgery News (Jan. 15, 1992), pp. 55–58.

Primary Examiner—Randy C. Shay
Attorney, Agent, or Firm—Jeffrey S. Schira

[57] ABSTRACT

A one-piece polymethylmethacrylate intraocular lens having an optic with an optic profile and a pair of haptics each extending from the optic within the optic profile and each with a medial segment of variably reduced cross-sectional area.

33 Claims, 3 Drawing Sheets

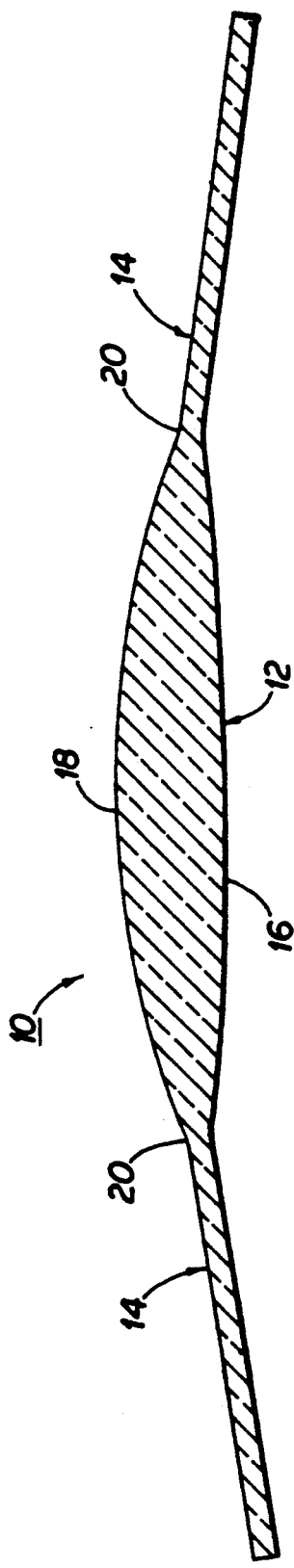
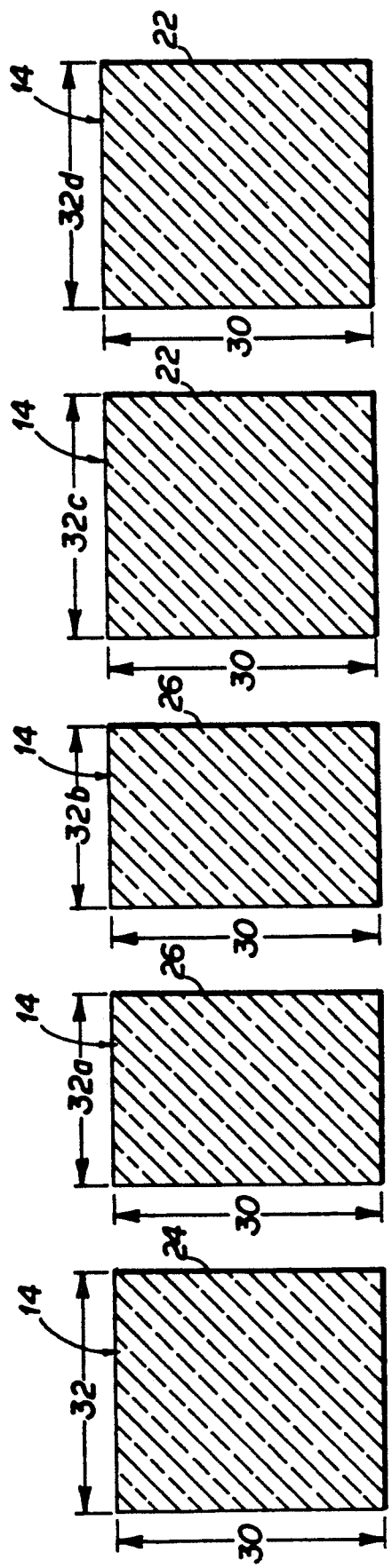

INTRAOCULAR LENS HAVING HAPTIC OF SPECIFIC CURVATURE AND PROPORTION

BACKGROUND OF THE INVENTION

The present invention relates to intraocular lenses and particularly to one-piece intraocular lenses.

For many years, the predominant method of treating a cataractous lens is to remove the diseased lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Both surgical procedures require that the anterior lens capsule be cut to allow access to the lens itself and to allow the implantation of the replacement lens, and because the capsule bag is used to hold or retain the IOL in place after surgery, the opening should be as small as possible. Although extracapsular cataract extraction has been the preferred surgical technique, phacoemulsification is becoming increasingly popular, in part because of the relatively small (3–3.5 millimeter) tunnel incision that can be used with phacoemulsification.

A typical IOL comprises an artificial lens ("optic") and at least one support member ("haptic") for positioning the IOL within the capsular bag. The optic may be formed from any of a number of different materials, including polymethylmethacrylate (PMMA), polycarbonate and acrylics, and it may be hard, relatively flexible or even fully deformable so that the IOL can be rolled or folded prior to insertion. The haptics generally are made from some resilient material, such as polypropylene or PMMA. IOL's may be characterized as either "one-piece" or "multi-piece." With one-piece IOL's, the haptic and the optic are formed integrally as a blank and the IOL is then milled or lathed to the desired shape and configuration. The multi-piece IOL's are formed either by attaching the haptic to a pre-formed optic or by molding the optic around the proximal end of the haptic.

IOL's generally are designed with three criteria in mind; optical clarity, centration within the capsular bag and ease of surgical implantation. While current plastics such as PMMA have excellent clarity, the goals of ease of implantation at all surgical skill levels) and centration have been difficult to obtain consistently. Although ease of insertion is less of a concern when the surgical technique used is extracapsular extraction (with its relatively large incision), ease of insertion is extremely important with the small tunnel incision increasingly used with phacoemulsification. The designs of current IOL's generally trade off some insertion ease for improved centration without deformation and visa versa. For example, one predominant style of IOL includes a "J" or buttonhook-shaped haptic that is relatively easy to implant. However, the curled base of the J-shaped haptic contacts the capsular bag along only a very short radius, and tends to stretch and distort the capsular bag, resulting in zonular dialysis and possible optic displacement. The other predominant style of IOL includes a more gently curved, C-shaped haptic that contacts the capsular bag over a longer radius and tends not to induce capsular bag distortion to the same extent as J-shaped haptics. However, C-shaped haptics generally project outwardly from the diameter of the optic and, therefore, must fold backward over the optic during insertion. The relatively long length of C-shaped haptics requires that they be made relatively stiff to ensure centration, and this stiffness causes the haptic to resist bending or folding that when combined with the projection of the haptic over the optic, can cause the haptic to grab the wound tissue, making IOL's with C-shaped haptics relatively difficult to implant in the capsular bag when compared to J-shaped haptics, especially through the increasingly preferred small tunnel incision and small capsulorhexis used in phacoemulsification.

Many IOL designs have been developed in an effort to obtain an IOL that has excellent centration and is easy to implant. For example, U.S. Pat. Nos. 4,585,455, 4,608,049, 4,664,665, 4,664,667, 4,725,277, 4,731,079, 4,816,031 and 4,822,358 disclose an IOL having a thickened haptic attachment point and an enlarged or bulbous distal haptic tip. However, none of these patents discloses an IOL having a relatively flexible haptic or a haptic having a medial hinge or joint, and they all rely on the roundness of the bulbous tip to reduce tissue grabbing during insertion.

U.S. Pat. Nos. 4,446,581 and 4,676,794 disclose an IOL having a coil spring in the medial segment of the haptic to allow the haptic to flex. However, the distal segments of the haptic disclosed in these patents bow toward the optic. Therefore, there is minimal contact between the haptic and the capsular bag and capsular bag distortion can result.

U.S. Pat. Nos. 4,701,181, 4,710,195, 4,725,277, 4,932,967 and Re. 33,039 disclose IOL's having haptics with a medial segment of reduced cross-section area. However, the haptics disclosed in these patents all extend beyond the optic profile, requiring the incision to be enlarged to accommodate the haptics or risk potential haptic damage or excessive tissue (wound) contact.

U.S. Pat. Nos. 4,418,431, 4,504,981, 4,568,347, 4,575,374, 4,581,033, 4,591,358, 4,655,775, 4,828,558, 4,863,465 and 4,871,363 disclose IOL's having haptics with an elbow or "knee" joint to allow the haptic to flex more easily. However, none of these patents discloses the use of an elbow or knee joint of reduced cross-sectional area. These haptic are all relatively stiff, and rely on the geometry of the elbow or knee to facilitate flexing of the haptic.

U.S. Pat. No. 4,990,159 discloses an IOL with haptics having alternating cross-sectional area. While the design of the haptics in this patent may allow for more flexing of the haptic, this flexure is uniform across the entire length of the haptic and does not necessarily ensure that the haptics contact the capsular bag along a large radius. Furthermore, the haptic disclosed in this patent extends beyond the optic profile.

Another multi-piece IOL distributed briefly during the late 1970s by Medicornea Intraocular had a pair of squarely bent, modified C-shaped or L-shaped haptics. While the haptics on this lens appear to contact the capsular bag along a longer length of the haptic than the typical C-shaped haptic, the sharp corners and shape of the haptic made insertion difficult. In addition, the haptics have the same cross-section throughout their entire lengths, reducing flexibility. The disadvantages of this design are not surprising considering the fact that in the late 1970s, phacoemulsification was in its infancy and the predominant surgical technique for cataract removal was extracapsular extraction with sulcus placement of the IOL and centration rather than ease of insertion was the primary concern of the IOL designer.

Accordingly, a need continues to exist for an IOL having a haptic that tensions the capsular bag evenly and without deformation and that can be inserted more easily through the small tunnel incision used in phacoemulsification.

BRIEF SUMMARY OF THE INVENTION

The present invention improves upon prior art intraocular lenses by providing an intraocular lens having a haptic with a shallowly curved or L-shaped distal end and a reduced diameter medial section that acts like an elbow joint or spring hinge to allow the haptic to expand outwardly after insertion to contact more fully and to tension more evenly the capsular bag, permitting increased contact between the haptics and the capsular bag irrespective of capsular bag size. A relatively thick proximal section resists flexing and helps to guide the IOL through the incision. In addition, the haptic origins and ends are interior of the optic diameter so that no part of the haptic extends beyond the optic profile.

Accordingly, one objective of the present invention is to provide an intraocular lens that is relatively easy to insert in small incisions.

Another objective of the present invention is to provide an intraocular lens with haptics that do not project beyond the optic profile.

Another objective of the present invention is to provide an intraocular lens with haptics having haptic origins that are interior of the optic diameter.

Another objective of the present invention is to provide an intraocular lens having improved contact between the haptic and the capsular bag, irrespective of capsular bag size.

Another objective of the present invention is to provide an intraocular lens having a haptic with improved flexibility.

Another objective of the present invention is to provide an intraocular lens having a hinged haptic.

Another objective of the present invention is to provide an intraocular lens having a haptic with a medial segment with reduced cross-sectional area.

Still another objective of the present invention is to provide an intraocular lens that reduces capsular bag distortion.

A further objective of the present invention is to provide an intraocular lens that resists displacement within the capsular bag.

These and other objectives and advantages of the present invention will become apparent from the detailed description, drawings and claims that follow.

BRIEF DESCRIPTION OF THE DRAWING

FIG. 2 is a cross-sectional view of the intraocular lens illustrated in FIG. 1 taken along line 2—2.

FIG. 3 is a cross-sectional view of the haptic of the intraocular lens illustrated in FIG. 1 taken along line 3—3.

FIG. 4 is a cross-sectional view of the haptic of the intraocular lens illustrated in FIG. 1 taken along line 4—4.

FIG. 5 is a cross-sectional view of the haptic of the intraocular lens illustrated in FIG. 1 taken along line 5—5.

FIG. 6 is a cross-sectional view of the haptic of the intraocular lens illustrated in FIG. 1 taken along line 6—6.

FIG. 7 is a cross-sectional view of the haptic of the intraocular lens illustrated in FIG. 1 taken along line 7—7.

DETAILED DESCRIPTION OF THE INVENTION

Figure 1:
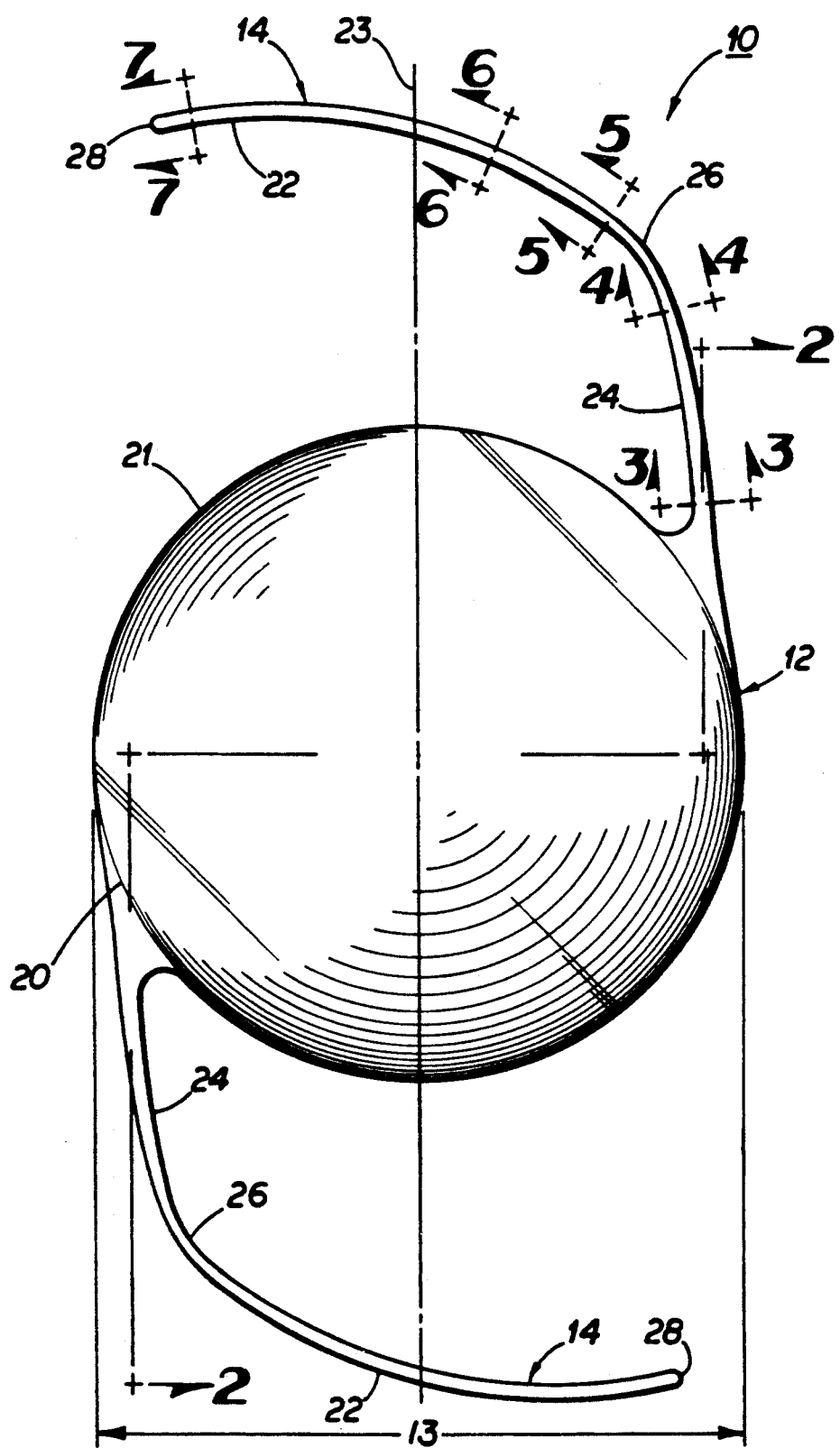
FIG. 1 is a plan view of the intraocular lens of the present invention.
Figure 10:
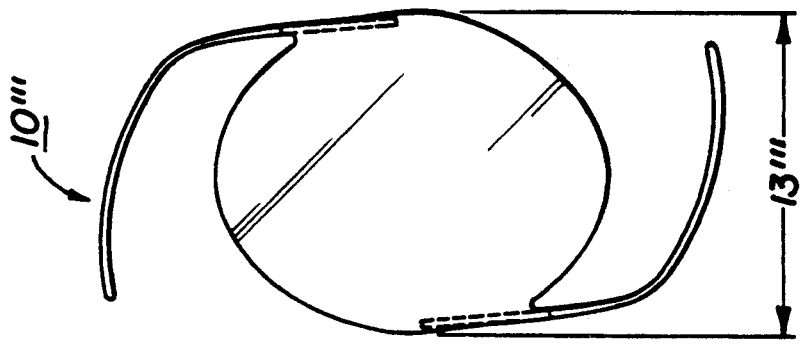
FIG. 10 is a plan view of a fourth embodiment of the intraocular lens of the present invention.
Figure 9:
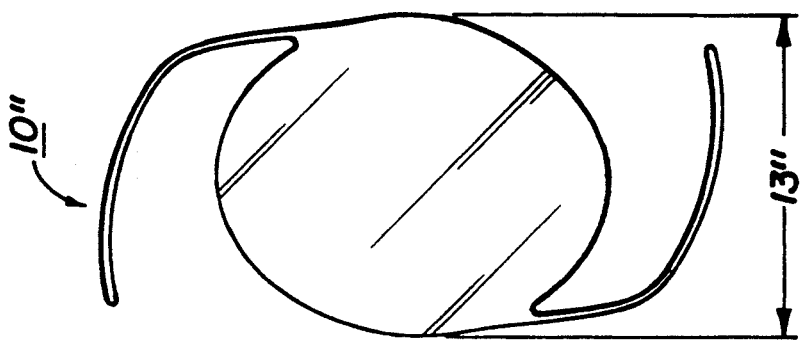
FIG. 9 is a plan view of a third embodiment of the intraocular lens of the present invention.
Figure 8:
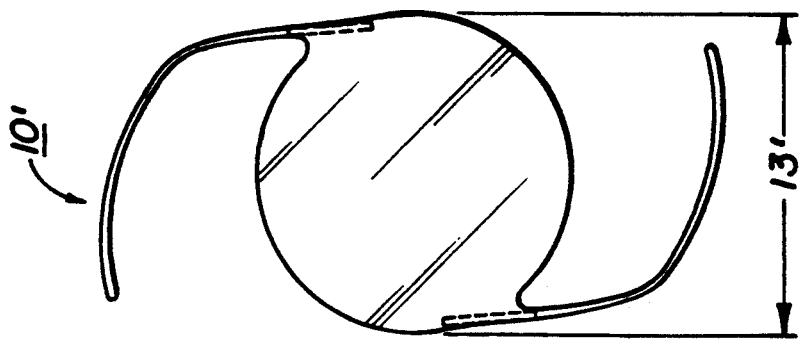
FIG. 8 is a plan view of a second embodiment of the intraocular lens of the present invention.

As can be seen in FIGS. 1 and 2, IOL 10 of the present invention includes an optic 12 and at least one haptic 14. Optic 12 has anterior face 16 and posterior face 18 that may be of any suitable shape or design, such as concave, convex, biconvex, plano-convex, concave-convex, multifocal or toric. Optic 12 may be made of any suitable, biocompatible plastic, such as PMMA, polycarbonate, acrylics or copolymers of esters of acrylic acid and methacrylic acid, may contain a material for absorbing ultraviolet light, for absorbing blue light (such as a yellow, yellow-brown, orange or brown pigment) or for attenuating the transmission of any desired visible wavelength and may be circular as shown in FIGS. 1, 2 and 8, elliptical or oval as shown in FIGS. 9 and 10 or a closed curve of any suitable design. Optic 12 is approximately between 4.5 and 7.0 millimeters (mm) in diameter with 5.75 mm being preferred.

IOL 10 may be either a one-piece as shown in FIGS. 1, 2 and 8 or a multi-piece lens as shown in FIGS. 8 and 10 but preferably is one-piece with haptics 14 formed integrally with optic 12 from a solid blank of material that is milled or lathed to the desired shape and cross section. Haptics 14 project radially outward longitudinally from haptic origin 20 on optic 12 so that the distance of distal segment 22 lies at a greater distance from optic 12 than medial segment 26 or proximal segment 24 yet all of haptic 14 remains within optic profile or width 13, 13', 13", or 13'" of optic 12. In order to provide capsular bag contact along the entire length of distal segment 22, the total diameter of IOL 10, from haptic tip 28 to haptic tip 28 must be approximately between 10.5 mm and 12.5 mm with approximately 12.0 mm being preferred. This provides the best fit of IOL 10 in the average 9.1 mm to 9.9 mm capsular bag.

As can be seen in FIG. 1, proximal segment 24 is relatively straight, approximately 1.7 mm long and has a radius of curvature of approximately 21.5 mm; medial segment 26 is tightly curved, approximately 0.5 mm long and has a radius of curvature of approximately 1.30 mm; and distal segment 22 is slightly curved, approximately 4.7 mm long and has a radius of curvature of approximately between 4.50 and 5.00 mm. Haptic origin 20 is preferably on a point of the peripheral edge 21 where width 13, 13', 13", or 13'" is not at its maximum, and proximal segment 24 preferably projects slightly inward toward centerline 23 of optic 12 so that no part of haptic 14 extends beyond optic width 13, 13', 13", or 13'". This placement of haptic origin 20 and the inward projection of proximal segment 24 help to prevent haptic 14 from grabbing the wound tissue, thereby easing the insertion of IOL 10 into the capsular bag. In addition, the relative stiffness of proximal segment 24, as compared to medial segment 26, helps a to guide IOL 10 through the incision.

As can be seen in FIGS. 3–7, thickness 30 of haptic 14 remains constant from haptic origin 20 to tip 28, for example, 0.17 mm, but the width 32 of haptic 14 varies, narrowing between haptic origin 20 and medial segment 26 and widening between medial segment 26 and tip 28 so that medial segment 26 is the narrowest part of haptic 14. As can be seen in FIGS. 3 and 7, height 30 of haptic 14 at haptic origin 20 and tip 28 is approximately the same, with a width of approximately 0.17 mm. However, width 32 of haptic 14 decreases along the length of proximal segment 24 so that, as can be seen in FIG. 4, width 32a of proximal segment 24 at medial segment 26 is only approximately between 0.16 mm and 0.14 mm, 0.14 mm being preferred. Width 32 continues to narrow along the length of medial segment 26 so that, as can be seen in FIG. 5, width 32b of medial segment 26 at is narrowest point is only approximately 0.12. As can be seen in FIGS. 6 and 7, width 32 of haptic 14 increases along the distal portion of medial segment 26 so that at the intersection of medial segment 26 and distal segment 22, width 32c is approximately 0.14 mm. Width 32 of haptic 14 remains constant for the entire length of distal segment 22 so that at tip 28, width 32d remains approximately 0.14 mm. Maintaining a constant thickness 30 along the entire length of haptic 14 while having a varying width 32 from haptic origin 20 to tip 28 allows haptic 14 to flex, but this flexing is primarily limited to planar flexing within or parallel to the plane of optic 12 and flexing of haptic 14 in the plane normal to the plane of optic 12 is minimized. In addition, the relative stiffness of distal segment 22 and proximal segment 24 compared to medial segment 26 causes haptic 14 to flex primarily along medial segment 26. Thus, medial segment 26 acts like a hinge allowing distal segment 22 to expand outwardly once IOL 10 is fully inserted into the capsular bag. The relatively shallow radius of distal segment 22 causes haptic 14 to contact the capsular bag along the entire length of distal segment 22, resulting in even tensioning of the capsular bag due to the broad arc of contact. Although FIGS. 3–7 illustrate haptic 14 with a rectangular cross-section, other suitable cross-sectional shapes, such as rectangular with rounded corners, oval or elliptical, may also be used This description is given for purposes of illustration and explanation. It will be obvious to those skilled in the relevant art that modifications may be made to the invention as described herein without departing from its scope or spirit.

I claim:

1. An intraocular lens, comprising:
   a. an optic having a width and a length perpendicular to said width; and
   b. at least one haptic extending from the optic such that it does not intend beyond the width of the optic, the at least one haptic having
      i. a proximal segment having a first length and a radius of curvature of approximately 21.5 millimeters,
      ii. a distal segment having a second length that is approximately 2.8 times the first length and having a radius of curvature of between 4.5 millimeters and 5.0 millimeters and
      iii. a medial segment of varying cross-sectional area having a radius of curvature of approximately 1.3 millimeters.
2. The intraocular lens of claim 1 wherein the optic is approximately between 4.5 and 7.0 millimeters in diameter.
3. The intraocular lens of claim 2 wherein the optic is approximately 5.75 millimeters in diameter.
4. The intraocular lens of claim 1 wherein the lens is approximately between 10.5 and 12.5 millimeters in diameter.
5. The intraocular lens of claim 1 wherein the overall length of the lens is approximately between 10.5 and 12.5 millimeters.
6. The intraocular lens of claim 1 wherein the optic and the haptic comprise polymethylmethacrylate.
7. The intraocular lens of claim 1 wherein a shape of the optic is a closed curve.
8. The intraocular lens of claim 7 wherein the closed curve is a circle.
9. The intraocular lens of claim 7 wherein the closed curve is an ellipse.
10. The intraocular lens of claim 7 wherein the closed curve is an oval.
11. The intraocular lens of claim 1 wherein the medial segment has a variable cross-sectional area of approximately between 0.04 and 0.01 square millimeters.
12. The intraocular lens of claim 1 wherein the lens comprises a one-piece lens.
13. The intraocular lens of claim 1 wherein the lens comprises a multi-piece lens.
14. A one-piece, polymethylmethacrylate intraocular lens, comprising:
    a. an optic having a width and a length perpendicular to joint width; and
    b. a pair of haptics each extending from the optic such that they do not extend beyond the width of the optic and each haptic having
       i. a proximal segment having a first length and a radius of curvature of approximately 21.5 millimeters,
       ii. a distal segment having a second length that is approximately 2.8 times the first length and having a radius of curvature of between 4.5 millimeters and 5.0 millimeters and
       iii. a medial segment of varying cross-sectional area having a radius of curvature of between approximately 1.3 millimeters.
15. The intraocular lens of claim 14 wherein the optic is approximately between 4.5 and 7.0 millimeters in diameter.
16. The intraocular lens of claim 15 wherein the optic is approximately 5.75 millimeters in diameter.
17. The intraocular lens of claim 14 wherein the lens is approximately between 10.5 and 12.5 millimeters in diameter.
18. The intraocular lens of claim 17 wherein the overall length of the lens is approximately 12.0 millimeters.
19. The intraocular lens of claim 14 wherein a shape of the optic is a closed curve.
20. The intraocular lens of claim 19 wherein the closed curve is a circle.
21. The intraocular lens of claim 19 wherein the closed curve is an ellipse.
22. The intraocular lens of claim 19 wherein the closed curve is an oval.
23. The intraocular lens of claim 14 wherein the medial segments have a variable cross-sectional area of approximately between 0.04 and 0.01 square millimeters.

24. A multi-piece intraocular lens, comprising:
 a. an optic having a width and a length perpendicular to said width; and
 b. a pair of haptics each extending from the optic such that they do not extend beyond the width of the optic and each haptic having
  i. a proximal segment having a first length and a radius of curvature of approximately 21.5 millimeters,
  ii. a distal segment having a second length that is approximately 2.8 times the first length and having a radius of curvature of between 4.5 millimeters and 5.0 millimeters and
  iii. a medial segment of varying cross-sectional area having a radius of curvature of approximately 1.3 millimeters.

25. The intraocular lens of claim 24 wherein the optic is approximately between 4.5 and 7.0 millimeters in diameter.

26. The intraocular lens of claim 25 wherein the optic is approximately 5.75 millimeters in diameter.

27. The intraocular lens of claim 24 wherein the lens is approximately between 10.5 and 12.5 millimeters in diameter.

28. The intraocular lens of claim 27 wherein the overall length of the lens is approximately 12.0 millimeters.

29. The intraocular lens of claim 24 wherein a shape of the optic is a closed curve.

30. The intraocular lens of claim 29 wherein the closed curve is a circle.

31. The intraocular lens of claim 29 wherein the closed curve is an ellipse.

32. The intraocular lens of claim 29 wherein the closed curve is an oval.

33. The intraocular lens of claim 24 wherein the medial segments have a variable cross-sectional area of approximately between 0.04 and 0.01 square millimeters.

* * * * *

UNITED STATES PATENT AND TRADEMARK OFFICE
CERTIFICATE OF CORRECTION

PATENT NO. : 5,197,981

DATED : March 30, 1993

INVENTOR(S) : Southard

It is certified that error appears in the above-identified patent and that said Letters Patent is hereby corrected as shown below:

Column 5, line 3:  delete "a"
Column 5, line 60: delete "intend" and insert --extend--
Column 6, line 35: delete "joint" and insert --said--

Signed and Sealed this

Thirtieth Day of November, 1993

Attest:

BRUCE LEHMAN

Attesting Officer

Commissioner of Patents and Trademarks